United States Patent [19]

Reilly

[11] 4,370,982
[45] Feb. 1, 1983

[54] METHOD AND APPARATUS FOR INJECTING AND FOR CONTROLLING THE PRESSURE OF FLUID BEING INJECTED INTO A CATHETER

[75] Inventor: David M. Reilly, Glenshaw, Pa.

[73] Assignee: Medrad, Inc., Pittsburgh, Pa.

[21] Appl. No.: 185,737

[22] Filed: Sep. 10, 1980

[51] Int. Cl.³ .......................................... A61M 25/00
[52] U.S. Cl. ........................................ 604/98; 92/52; 604/99; 604/100
[58] Field of Search ............... 188/348, 234, 235, 236, 188/218 R, 218 C, 218 PA, 218 P; 73/744, 714; 92/52, 51, 5 R, 65, 66

[56] References Cited

U.S. PATENT DOCUMENTS

| 3,055,371 | 9/1962 | Kulick | 128/325 |
| 3,904,416 | 9/1975 | Onada et al. | 92/65 X |
| 4,195,637 | 4/1980 | Gruntzig et al. | 128/349 B X |
| 4,244,366 | 1/1981 | Raines | 128/218 C |

Primary Examiner—Stephen C. Pellegrino
Attorney, Agent, or Firm—Fleit & Jacobson

[57] ABSTRACT

An apparatus for measuring and detecting the pressure in a fluid being injected into a closed system, for instance, fluid being injected into a dilitation catheter, such as a balloon catheter used for the purpose of percutaneous transluminal angioplasty. The apparatus provides a pressure measuring system that includes a housing for releasably and slidably holding the barrel of a syringe used to deliver fluid into the balloon catheter; and a device for measuring and indicating fluid pressure in the syringe barrel, which is also the balloon pressure. The pressure measuring system indirectly measures pressure changes of fluid within the syringe barrel by sensing movement of the barrel as a result of fluid pressure changes. Since a pressure change is sensed by sensing movement of the syringe barrel, the only parts of the system directly contacted by the fluid inflating the balloon are the syringe barrel and syringe plunger. A control device for controlling movement of a piston within the syringe barrel also is provided. The control device makes it possible to slowly or quickly increase or decrease fluid pressure and facilitates maintenance of a desired pressure.

18 Claims, 16 Drawing Figures

METHOD AND APPARATUS FOR INJECTING AND FOR CONTROLLING THE PRESSURE OF FLUID BEING INJECTED INTO A CATHETER

BACKGROUND OF THE INVENTION

1. Field of the Invention

The present invention provides an apparatus and method for injecting fluid into a balloon catheter and a device for controlling the rate and pressure of fluid injection. Such catheters, when inflated by the injected fluid, are conventionally used for the purpose of percutaneous transluminal angioplasty.

Angioplasty is a procedure for dilating arteries which are occluded or blocked. It is done primarily on femoral (thigh) and renal (kidney) obstructions, and in some cases on coronary artery obstructions. A special catheter is used which contains a sausage-shaped segment or balloon at the distal end. To re-shape an occluded artery, the balloon portion is inflated, for instance, by being filled and pressurized with diluted contrast media.

2. Description of the Prior Art

An early practitioner of the angioplasty procedure was Dr. Andreas Gruntzig of the University of Zurich. The procedure developed by Dr. Gruntzig uses a special double lumen catheter. The first lumen allows passage of a guide wire and contrast media, like a conventional catheter. The second lumen connects to a sausage-shaped segment or balloon at the distal end of the catheter, which is generally filled and pressurized with diluted contrast media. Briefly, the procedure involves inserting a guide wire into a blood vessel to be dilated and advancing the guide wire to and past the block. Next, a balloon catheter is inserted along the guide wire and advanced to the most distal portion of the block or occlusion. Then, the balloon is inflated to reform the blockage material against the artery wall. The dilated balloon creates a smooth increased-diameter inner lumen in the artery. After dilation, the balloon is collapsed and retracted. The site of the former obstruction is examined, and, if necessary, the procedure is repeated until the entire segment of the artery is dilated.

The purpose of an angioplasty injector is to make the balloon inflation task easier and safer. One conventional procedure is to use a syringe to expand the balloon with radiopaque dye, while watching the balloon on an x-ray monitor. An operator proceeds by judging the relative balloon size, without knowing the balloon pressure; however, the balloon may rupture if its bursting pressure is exceeded.

A first approach to solving the problem of measuring the pressure of fluid inflating the balloon, i.e., syringe fluid pressure, is to interpose a T-fitting between the delivery end of the syringe and the balloon. A tire pressure-type gauge or other pressure indicator is connected to the T-fitting in such manner that the gauge comes in direct contact with the fluid, as it leaves the syringe, and measures the pressure exerted by the fluid.

One such system uses a slider that moves out of a housing with an increase in pressure and retracts into the housing with a decrease in pressure. Since a moving part of the gauge directly contacts the media solution, cleaning and sterilization of the gauge is required.

A second approach using a T-fitting for measuring syringe fluid pressure is to interpose a gauge using a separate pressure sensing member or disposable diaphragm positioned between the delivery end of the syringe and the balloon. One end of the diaphragm is contacted by the media fluid entering the balloon, while the other end acts on a pressurizing fluid associated with a gauge. This approach, like the first approach, uses a member directly contacted by the media fluid.

A problem encountered with use of a T-fitting or with use of a pressure sensing member directly contacted by the contrast media solution is that the contrast media solution used to inflate the balloon must be removed by thorough cleaning after each use. Such cleaning involves disassembly, cleaning, and sterilization. If the contrast media is not thoroughly removed, it becomes gummy as it dries, and, when fully dry, is hard like varnish. This can interfere with proper gauge operation. A gauge thus damaged could read improper pressures and mislead an operator.

A third approach to controlling media fluid pressure uses a pressurized carbon dioxide cartridge. The control system includes a pressure control, forward-reverse switch, and a conventional gauge arrangement. This approach uses a syringe and gauge that must be disassembled for cleaning. A problem with this approach is the need to provide a carbon dioxide cartridge, and the system can be expensive.

Several problems have been encountered with the previously described approaches. These problems include the need to carefully clean the measuring systems and gauges when the gauges or movable members associated with the gauges are directly contacted by the media fluid. Some of the approaches also require constant operator pressure on the syringe plunger to maintain dilation of the balloon. Some of the approaches rely solely on direct manual movement of the syringe plunger by the operator to obtain a desired pressure. With the exception of the system using the carbon dioxide cartridge, no provision is made for fine adjustment of pressure or for holding a desired pressure. Further, some of the gauges record only present pressure and do not record maximum inflation pressure achieved during an inflation cycle.

SUMMARY OF THE INVENTION

The present invention provides a method and apparatus for detecting and measuring the pressure of a fluid being injected into a closed system, such as a balloon catheter used for the purpose of percutaneous transluminal angioplasty. The invention also provides a device for controlling the rate of pressure change and for maintaining the pressure at a desired level.

The angioplasty injector provided by the present invention makes a balloon inflation task easier and safer than possible with previously known injectors. Since the inflation rate of the balloon can be controlled, there is less risk of balloon rupture.

The inventive angioplasty injector measures fluid pressure indirectly, so that the system is not contaminated by the media fluid used to inflate the balloon catheter. In order to accomplish such indirect measurement, the injector utilizes a sliding cylinder or annular member supported for movement with respect to a housing. The annular member supports a barrel of a syringe containing the fluid. One end of the syringe barrel is in fluid communication with the catheter, or other device to be inflated, and the other end is open to receive a plunger or piston. The piston is translatable with respect to the barrel to change the pressure of fluid contained in the syringe. When the pressure of the fluid is changed as a result of piston movement, there is a tendency of the barrel to move in the direction of movement of the piston. The syringe barrel is supported by the annular member in such manner that the annular member moves with the barrel. A sensing system is provided in the housing to sense movement of the annular member and to convert the sensed movement into a pressure reading.

Considering the invention in more detail, it provides a pressure sensing device for indirectly measuring the fluid pressure in a closed system. The pressure in the closed system is varied by the movement of a piston in a syringe barrel or other tubular member having a distal delivery end in fluid communication with the closed system and a flanged proximal end. The syringe barrel is held by a sliding cylinder of the pressure sensing device in such manner that pressure changes within the syringe barrel result in corresponding proportional movement of the barrel and sliding cylinder. The sliding cylinder preferably has an enlarged portion supported for sliding movement in a passageway extending through a housing. Another portion of the sliding cylinder is spaced from the passageway so that an annular space is formed therebetween. Seals are carried by the sliding cylinder for closing ends of the annular space. A pressure sensing means using the closed annular space is provided in the housing for sensing movement of the sliding cylinder. Such movement results from a tendency of the syringe barrel to move when pressure changes within the barrel, as a result of movement of a piston or plunger within the syringe barrel. The pressure sensing means includes first means for sensing and for generating a signal representative of movement of the sliding cylinder with respect to the housing and second means responsive to the first means for converting the signal into a pressure measurement. With one embodiment of the invention, the first means of the pressure sensing means uses the closed annular space. The sliding cylinder is movable by a flange at the proximal end of the syringe barrel so that one of the seals surrounding the sliding cylinder exerts pressure on a non-compressible fluid contained within a reservoir at least partially defined by the closed annular space. Changes in pressure within the reservoir volume are sensed and displayed by a gauge, the second means of the pressure sensing means. The gauge is designed to display both the current pressure sensed within the reservoir and the highest pressure reached during a given operating cycle.

The angioplasty injector is designed to receive and slidingly support a standard disposable syringe, such as a 10 ml syringe. Pressure in the syringe is measured indirectly so that components of the pressure measurement system are not contaminated by fluid within the syringe. More particularly, syringe pressure is measured by measuring the force pressing on the syringe plunger. For this purpose, the syringe barrel is slidingly supported and contained within an annular member or sliding cylinder. The sliding cylinder is disposed within a housing and surrounded by a fluid contained in a reservoir formed in the housing. The reservoir is sealed, and a gauge is connected to the reservoir to read the pressure of the contained fluid. When the syringe plunger exerts pressure on fluid in the syringe barrel to inflate the catheter, a force is also exerted on the syringe barrel. This force, in turn, is applied to the annular member, transmitted to the fluid contained in the reservoir, and sensed by the gauge. There is a direct relationship between the fluid pressure exerted by the syringe plunger on the fluid inflating the catheter and the pressure exerted on the fluid in the closed system surrounding the syringe barrel. Since there is no contamination of the gauge by the fluid being injected, cleaning of the gauge after an injection is greatly simplified.

Preferably, the injector is completely submersible and sterilizable with ethylene oxide gas and cold chemicals.

The invention also provides a drive mechanism or device for controlling movement of a piston with respect to a housing. The piston has an end protruding from the housing and is mounted for translational movement in a passageway formed in the housing. The device includes a holder having a portion thereof defining a passageway. The holder forms part of or is connectable to the housing in such manner that the passageway in the holder is parallel with the passageway in the housing. A threaded member is guided for movement by the passageway in the holder, and is engaged by a key connected to the holder so that rotation of the threaded member results in translation of the threaded member with respect to the holder. The threaded member and the piston are interconnected with each other for conjoint movement. The key preferably is movable into a position not contacting the threaded member to allow translational movement of the threaded member, without rotation. With such device, the piston is used to slowly or quickly expand a balloon, and to slowly or quickly deflate the balloon.

The invention, and its objects and advantages, will become more apparent in the detailed description of the preferred embodiments hereinafter presented.

DESCRIPTION OF THE PREFERRED EMBODIMENTS

The present description will be directed in particular to elements forming part of, or cooperating more directly with, the present invention. Elements not specifically shown or described herein are understood to be selectable from those known in the art.

Figures 1, 2, 3, 4, 5, 6:
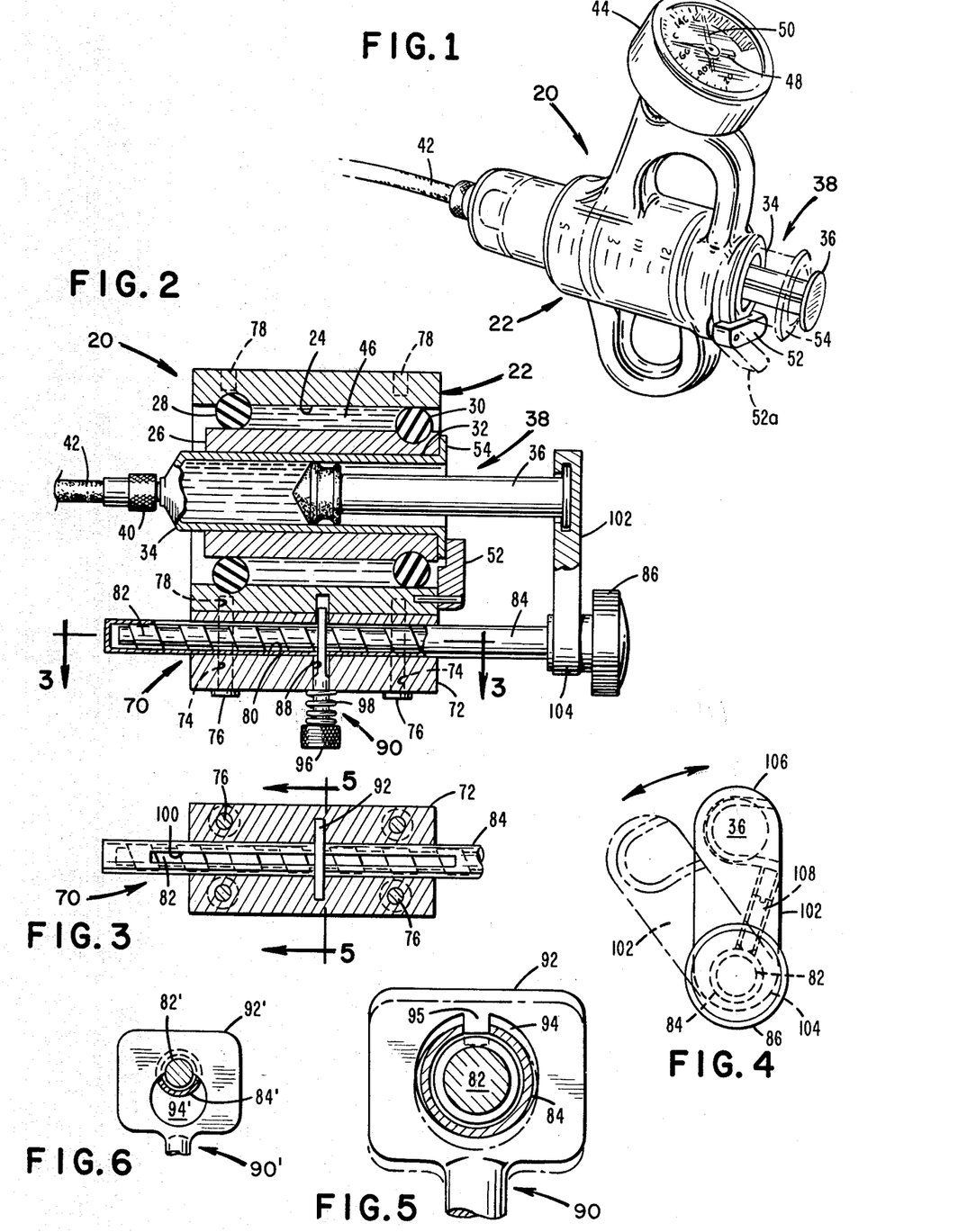
FIG. 1 is a perspective of one embodiment of an angioplasty injector according to the present invention.
FIG. 2 is a schematic sectional view of a modification of the embodiment of FIG. 1, including a drive mechanism for controlling movement of a syringe plunger.
FIG. 3 is a partial section along line 3—3 of FIG. 2.
FIG. 4 is a partial view, taken from the right, of the angioplasty injector of FIG. 2.
FIG. 5 is an enlarged view taken generally along line 5—5 of FIG. 3, with a bolt and sleeve of the injector in section.
FIG. 6 is an enlarged view, similar to FIG. 5, of a modification of a component of the present invention.

Referring now to the drawings, and to FIGS. 1 and 2 in particular, one embodiment of an angioplasty injector, generally designated 20, is illustrated. The injector illustrated in FIG. 2 is the injector of FIG. 1, modified to add a device for controlling movement of a syringe plunger with respect to the injector. Accordingly, the same reference numerals will be used in these figures.

The injector 20 has a housing, generally designated 22, having a passageway 24 formed therein. An axially-extending sliding cylinder or annular member 26 is held in a position spaced from the walls of the passageway 24 by O-ring seals 28 and 30. The member 26 has a central opening 32 forming a passageway through which a tubular member extends. Hereinafter, the tubular member will be referred to as a syringe barrel 34; however, it should be appreciated that the present invention is not limited to use only with syringes.

The combination of the syringe barrel 34 and plunger or piston 36 will be referred to as a syringe, which is generally designated 38. The distal end 40 of the syringe barrel 34 is connected to the proximal end of a lumen of a balloon catheter, a portion of which, designated 42, is illustrated. Movement of syringe piston or plunger 36 within the syringe barrel 34 results in injection into or withdrawal from the balloon catheter 42 of a pressurizing fluid, such as a dilute contrast media. In addition, build-up of pressure within the syringe barrel 34 resulting from movement of the syringe plunger 36 towards the distal end 40 of the barrel results in a corresponding tendency of the barrel 34 to move towards the distal end. By sensing the tendency of the barrel to move, it is possible to measure the pressure of the fluid within the barrel, without the measuring device actually coming into contact with the fluid pressurizing the catheter.

As will be discussed in more detail hereinafter, a pressure gauge 44 is in communication with a reservoir 46 formed within the housing 22 between portions of the wall of the housing defining the passageway 24, the O-ring seals 28, 30, and portions of the outer wall of the annular member 26. The gauge 44 provides a visual indication of pressure changes occurring within the fluid contained in the syringe 38. For this purpose, the gauge 44 preferably has a first needle 48 that provides a visual indication of the current pressure and a second needle 50 that provides a visual indication of the maximum pressure attained during a given inflation or injection sequence. Preferably, one of the needles 48, 50 has a projecting tab that is engaged by the other needle so that the needles move together in the clockwise direction, with reference to the device illustrated in FIG. 1, and only the needle 48 moves in the counter-clockwise direction when pressure drops within the reservoir 46. After the termination of a given injection procedure, the needle 50 is manually reset in preparation for the next injection procedure. Preferably, the syringe 38 and the housing 22 are releasably interlocked with each other. For this purpose, a recessed latch or locking member 52 is pivotally connected to a rear portion of the housing 22. The locking member 52 is movable between a first position 52a, as illustrated in phantom lines in FIG. 1, and a second position, as illustrated in solid lines. When the member 52 is in the first position, a syringe barrel 34 is insertable into and removable from the passageway 32 formed in the annular member 26 located within housing 22. When the member 52 is in the second position, it releasably interlocks a flange 54 of the syringe barrel 34 with the annular member 26 and the housing 22. When the locking member 52 is in the second position, any tendency of the syringe barrel 34 to move as a result of pressure variations within the fluid contained in the barrel will be sensed and displayed on the gauge 44.

As can be seen from FIG. 2, the reservoir 46 has an inner wall defined by an outer wall of the annular member 26, an outer wall defined by a portion of the walls of the housing forming the passageway 24, and end walls defined by the seals 28, 30. The seal 30 is positioned in a groove in the annular member so that translation of the annular member results in a pressure change within the reservoir 46. The seal 28 is positioned in a groove in the passageway 24 so that the annular member 26 is movable with respect to seal 28.

Figures 7, 8, 9, 10, 11, 12, 13:
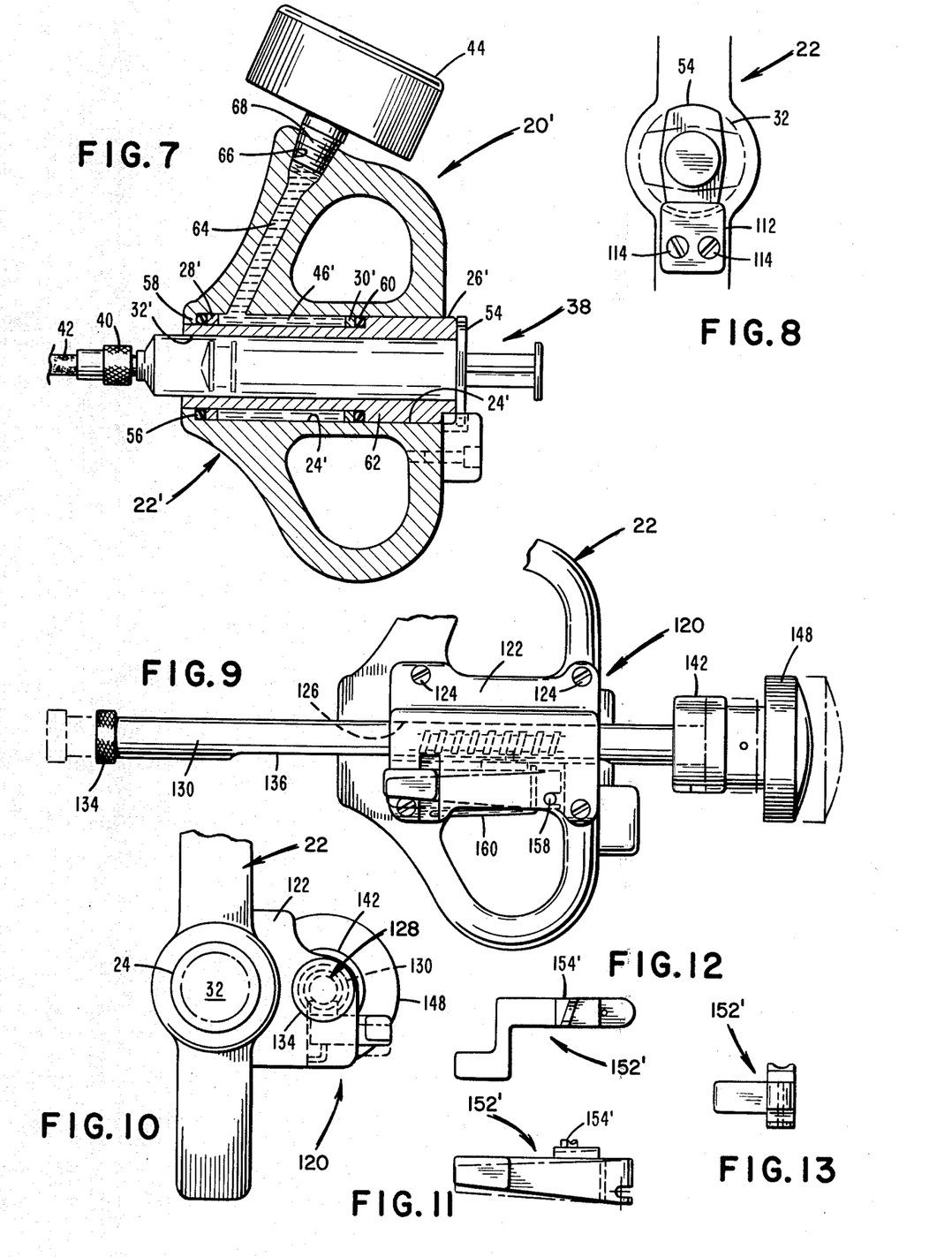
FIG. 7 is a partial longitudinal section of a modification of the embodiment of FIG. 1.
FIG. 8 is a partial view, taken from the right of FIG. 7, of a further modification of the present invention.
FIG. 9 is a schematic top plan view of one embodiment of a syringe drive mechanism attached to an angioplasty injector of the type illustrated in FIG. 1.
FIG. 10 is a schematic front view of the syringe drive mechanism and injector of FIG. 9.
FIG. 11 is a top view of an embodiment of an engager button used with the syringe drive mechanism of FIG. 9.
FIG. 12 is a side view of the engager button of FIG. 11.
FIG. 13 is an end view of the engager button of FIG. 11.

Referring now to FIG. 7, the elements of a modified embodiment of the present invention that sense and display pressure variations within the syringe barrel 34 will be described. The same reference numerals will be used to identify components already described in conjuction with the description of FIGS. 1 and 2. The same reference numerals, with primes attached, will be used to identify similar components.

In FIG. 7, a sliding hollow cylinder or axially extending annular member 26' is positioned within the housing 22' and has an inner surface defining the passageway 32' and an outer surface of a reduced diameter distal portion defining a wall of the reservoir 46'. The reservoir 46' is further defined by an interior surface of the housing 22' forming the passageway 24'. A first O-ring seal 28' is positioned between a balance seal 56 and the reservoir 46'. A shoulder 58 of the housing projects inwardly to limit forward movement of the seals 28' and 56. A second 0-ring 30' is positioned between the reservoir 46' and a balance seal 60. A shoulder 62 projects outwardly from the annular member 26' to form a seat for the balance seal 60. The shoulder 62, which forms an enlarged diameter proximal end of the cylinder 26', also engages the passageway 24' to guide sliding movement of the member 26' with respect to the housing 22'. A passageway 64 extends from the body of the reservoir 46' to an exterior surface of the housing 22' and has a threaded outer portion 66 that receives a threaded portion 68 of the pressure gauge 44. The reservoir 46' is filled with a non-compressible fluid, such as silicon oil, through the passsageway 64 prior to the connection of the gauge 44 to the housing 22'. Alternatively, or in addition, a separate fitting (not shown) is provided for filling the reservoir 46'. After the reservoir has been filled with a non-compressible fluid, movement of annular member 26' to the left, with respect to FIG. 7, will be opposed by fluid pressure in the reservoir acting on the O-ring 30'. Thus, movement of annular member 26' will result in corresponding pressure changes in the reservoir 46', which changes will be sensed and displayed by the gauge 44.

Since there is relative movement between the annular member 26' and the housing 22', the O-ring seals, in conjunction with the balance seals, must be designed to slidingly seal the reservoir 46'. Seals made of TEFLON material have been found suitable for this purpose. Also, it is possible to replace the seals with bellows.

With one embodiment of the invention, the sliding cylinder or annular member 26' is designed to move approximately 1/32-inches when the pressure of the fluid in the syringe barrel changes from approximately 1 to approximately 10 bars (150 psi). Also, the volume of the reservoir is approximately 8 cc.

The operation of the basic system will now be explained with respect to FIG. 2. First, it is assumed that the syringe barrel 34 is half-full of fluid and that the balloon catheter 42 also contains fluid. When the plunger 36 moves towards the distal end 40 of the syringe barrel 34, additional syringe fluid is forced into the balloon 42 thereby expanding the balloon. The pressure exerted by the syringe fluid on the syringe barrel 34 causes the barrel 34 to tend to move or exert a force in the direction of movement of the plunger. The syringe heel 54 pushes on the sliding cylinder or annular member 26' thereby causing the member 26' and O-ring 30 to move slightly in the direction of movement of the syringe plunger, or piston. Movement of the O-ring 30 is opposed by a pressure build up in the fluid in reservoir 46'. The pressure change in the reservoir is sensed and registered on the gauge 44.

When it is desired to deflate the catheter 42, the piston 36 is moved away from the distal end 40 thereby relieving pressure within the system. The needle 50 indicates the maximum pressure applied prior to pressure release, while needle 48 measures pressure currently within the system. At the completion of an inflation operation, the locking member 52 is rotated to the position 52a so that the plunger heel 54 can be moved away from the housing 22. After the catheter 42 is disconnected from the distal end 40 of the syringe, the syringe is slid out of the housing and, if desired, discarded. Since the syringe, the only component of the angioplasty injector directly contacting the pressurizing media, preferably is disposable, clean up is greatly facilitated.

Referring now to FIGS. 2 to 5, a drive mechanism, generally designated 70, is illustrated. The drive mechanism 70 provides an advance-withdraw option for controlling movement of the syringe piston 36. When using the drive mechanism 70, an operator is able to propel the syringe plunger quickly for loading, for positioning the plunger before connecting the balloon catheter, or for quick filling of large balloons. Alternatively, the operator slowly advances the plunger to allow controlled filling and dilation of the balloon. Further, the balloon is slowly or quickly deflated. Since the balloon is blocking blood flow during the dilation procedure, it is generally advantageous to quickly deflate the balloon so blood flow can resume. Still further, when using the drive mechanism 70, balloon pressure is maintained at a desired level without continuous effort from the operator.

Considering now the drive mechanism 70 in greater detail, it includes a holder or housing 72 having a plurality of bores 74 formed therein for the passage of bolts 76. The injector housing 22 is formed on one or both sides with threaded bores 78 that receive threaded end portions of the bolts 76 to thereby interconnect the housings 22 and 72. Alternatively, the two housings are formed as one unit. The housing 72 has a passageway or bore 80 formed therein that is parallel to the passageways 24 and 32 when the housings 22 and 72 are interconnected. A threaded drive bolt 82, that is at least partially threaded, and, preferably, partially encased in a protective sleeve 84, is received in the passageway 80. A knurled knob 86 is connected to one end of bolt 82 in such manner that the knob is able to rotate the bolt within its protective sleeve 84.

A bore 88 is formed in the housing 72 that extends transversely to the bore 80. A plunger button or release button, generally designated 90, is disposed in the bore 88 and has, as illustrated in FIG. 5, an inner end 92 formed with an opening 94 for the passage of bolt 82 and its protective sleeve 84. The outer end 96 of the button 90 is biassed away from the housing 72 into an operative position by a spring 98. In the operative position, a shaped portion or key 95 protruding into the opening 94 engages the threads of bolt 82 so that rotation of the bolt 82 results in controlled translation of the bolt. When the outer end 96 is depressed against the spring bias, the inner end moves into an inoperative position, in which portions of the inner end surrounding the opening 94 are spaced from the threads of bolt 82. When the plunger button is in this position, the bolt 82 is translatable, with or without rotation. Preferably, portions of opening 94, although disengaged from bolt 82, are still engaged with sides of the opening 100 in sleeve 84 to prevent rotation of the sleeve within the passageway 80.

The drive mechanism 70 includes a lever or connector 102 for interconnecting the bolt 82 and the syringe piston 36 for conjoint movement. One end 104 of the lever is connected to or formed with a bushing for pivotal motion about the sleeve 84. The other end 106 of the lever has a shaped recess designed to mate with a flanged end of the piston 36 that is located outside of the syringe. A set screw 108 is provided friction to maintain the lever 102 in a desired position, such as, in engagement with the flanged end of the piston 36.

When the drive mechanism 70 is connected to the syringe piston 36 and the plunger button 90 is in the engaged position, an operator slowly increases or decreases pressure by turning knob 86. When knob 86 is turned, the screw or bolt 82 is translated with respect to the housing 72, the direction of translation depending on the direction turned. Piston 36 translates along with bolt 82 to provide controlled filling and deflating of the balloon. Also, the force exerted on the bolt by the plunger button 90, and other frictional forces, are sufficient to hold the shaft in a particular angular orientation without continuous effort from the operator. In this manner, a desired pressure is maintained within the catheter 42.

When it is desired to quickly inflate or deflate the catheter 40, plunger button 90 is moved to the disengaged position against the bias of spring 98. In this position, the interconnected screw 82 and piston 36 are rapidly movable, without a need to rotate the screw. When the outer end 96 of the plunger button 90 is released, the spring 98 causes the inner end 92 to re-engage with the screw 82. Thus, it is possible to alternate rapid, quick filling with slow, controlled filling.

FIG. 6 is an enlarged view of a modification of the structure illustrated in FIG. 5. Accordingly, the same reference numerals, with primes attached, will be used in conjunction with the description of FIG. 6.

FIG. 6 illustrates an inner end 92' of a release button 90'. An opening 94' is formed in the inner end for the passage of a threaded bolt 82' encompassed within a sleeve 84'. The opening 94' has an elongate opening portion extending inwardly 92'. The elongate portion is designed to be movable into and out of engagement with a threaded portion of the bolt 82'. When the release button 90' is in the position illustrated in FIG. 6, the elongate opening partially encompasses and engages grooves or portions between lands of the bolt 82', so that the bolt translates upon rotation thereof. When the button 90' is moved inwardly, the elongate portion of the opening is spaced from the lands of the bolt 82' so that the bolt translates without rotation. The elongate portion of the opening preferably remains within the slot formed in the sleeve 84' to prevent rotation of the sleeve 84'.

Referring now to FIG. 8, a modification of the locking member 52 is illustrated. The modified locking member, which is designated 112, is rigidly affixed to a portion of housing 22 by one or more screws 114. A portion of the locking member 112 extends over and partially blocks the opening or passageway 32. The protruding portion is recessed to lockingly receive the syringe flange 54.

With the embodiment of FIG. 8, a syringe barrel 34 is inserted into the opening 32 and positioned adjacent an outer end of the annular member 26. The barrel 34 is then rotated so that its flange 54 is positioned underneath the protruding portion of the locking member 112, thereby preventing removal of the syringe barrel from the housing.

Figures 14, 15, 16:
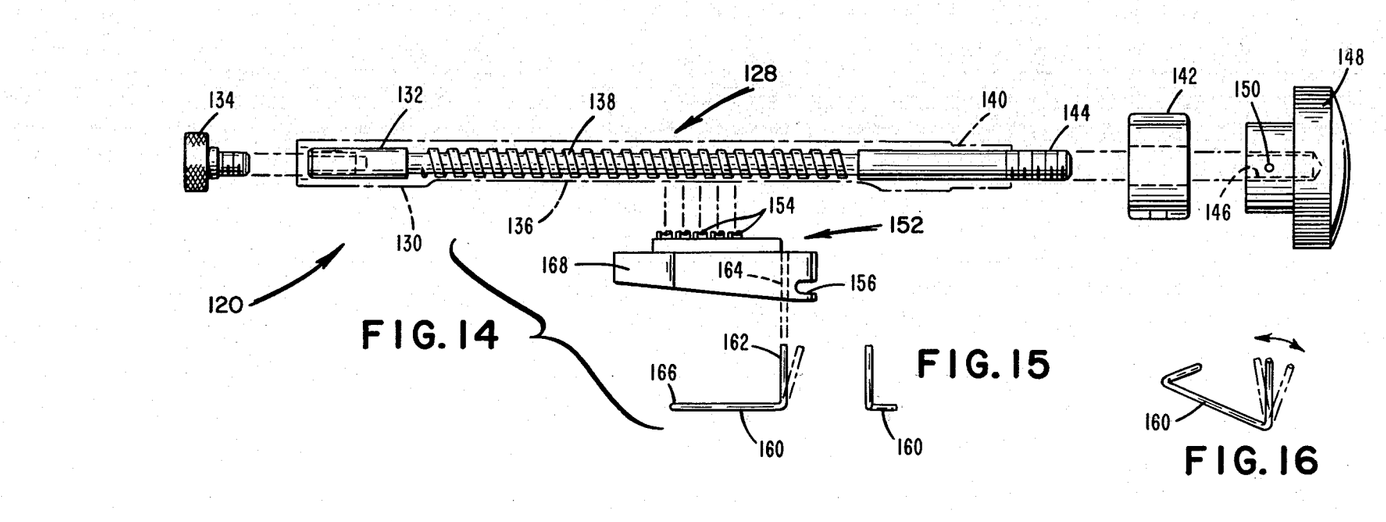
FIG. 14 is an exploded schematic view of the holder, or drive mechanism of FIG. 9, including a modification of the component illustrated in FIG. 11.
FIGS. 15 and 16 are additional views of a spring element illustrated in FIG. 14.

Referring now to FIGS. 9, 10, and 14, another embodiment of a drive mechanism, generally designated 120, connectable to the housing 22, is illustrated. As with the drive mechanism 70, the drive mechanism 120 includes a housing 122 that is connected by a plurality of screws 124 to the threaded bores 78 formed in the housing 22. The housing 122 has a bore 126 that is aligned with the passageways 24 and 32 when the housings 122 and 22 are interconnected. A bolt, generally designated 128, partially encompassed within a sleeve 130 is inserted into the bore 126. Use of the sleeve 130 is not required; however, use of the sleeve reduces risk of injury during rotation of the bolt 128 and enhances the overall appearance of the drive mechanism.

The bolt 128 has an internally tapped end portion 132 that receives a threaded knob or rod tube screw 132 used to hold the rod tube or sleeve 130 on the threaded rod or bolt 128. The sleeve 130 has a longitudinally-extending slit or opening 136 formed therein so that a threaded portion 138 of the bolt 128 is exposed. A stepped shoulder 140 is formed on an end of sleeve 130 for receiving a plunger engager 142. The engager 142 is similar to the previously described connector 102 and will not be described further. A threaded shaft 144 extends from the end of the bolt 128 into a bore 146 formed in a knurled knob 148. A set screw 150 is provided to interconnect the knob 148 and threaded portion 144 of bolt 128.

An engager button, generally designated 152, has a raised portion 154 thereof positioned within the housing 122, with the raised portion extending into the bore 126. The raised portion 154 has a plurality of shaped members designed to fit in grooves or between lands on the threaded portion 138 of the bolt 128. The botton 152 includes a recessed portion 156 that is engaged by a pin 158 to interconnect the button 152 and the housing 122. The button 152 is pivotable about the pin 158 to move the raised portion 154 into and out of engagement with the grooves on bolt 128. A spring 160 has one end portion 162 inserted into a bore 164 formed within the button 152 and an end portion 166 inserted into a bore formed within the housing 122. The spring is accessible from the exterior of the housing 122 to facilitate its insertion and removal. The spring 160 is shaped, in an operating position, to exert a biasing force on the button 152 so that the raised portions 154 are urged into engagement with threaded portion 138. An engagement portion 168 of the button 152 is positioned outside of the housing and is manually engageable to move the engager button 152 from the full line to the phantom line position illustrated in FIG. 9. When in the phantom line position, which is also a disengaged position, the portions 154 of the button 152 are disengaged from the threaded portion 138 of the bolt 128.

Referring now to FIGS. 11 to 13, a modified embodiment of the engager button 152 is illustrated. The modification, which is generally designated 152', is the same as the previously described engager button 152, except that the protruding portion 154' has only one member shaped to be positioned in the grooves on the threaded portion 138 of the bolt 128.

Since the drive mechanism 120 is designed to be screw-connected to the housing 22, it is possible to utilize the injector 20 with or without the drive mechanism 120. Also, the drive mechanism 120 is usable with other devices than the injector 20.

The assembly and operation of one embodiment of the present invention will now be described, for instance an embodiment combining the injector 20' illustrated in FIG. 7 with the drive mechanism 120 illustrated in FIG. 9. Initially, the drive mechanism 120 and the injector 20' are disassembled and all of the components cleaned. Annular member 26' is then inserted into the passageway 24' formed within the housing 22'. Reservoir 46' is filled with a suitable non-compressible fluid and the gauge 44 is screwed into the housing 22 to seal the reservoir and pressurize fluid within the reservoir. If necessary, the needles of the gauge are zero balanced. It is in this condition that the injector 20' is intended to be commercially marketed.

Next, the drive mechanism 120 is screw-connected to the housing 22'. A syringe 38 containing a fluid to be injected is then inserted into the opening 32' defined within the annular member 26'. If a locking mechanism of the type illustrated in FIG. 8 is used, the syringe barrel 34 is rotated to lock the flange 54 underneath the locking member 112. Alternatively, a locking member 52 is rotated, in the manner illustrated in FIG. 1. The distal end 40 of the syringe is then connected to the catheter 42 to be inflated.

In order to control the rate of movement of plunger 36, and thereby the rate of pressure buildup and balloon dilation, engager 142 is rotated into engagement with the end of plunger 36. Rotation of knob 148 then results in controlled translation of bolt 128 and sleeve 130 with respect to the housing 122 because of engagement of the portions 154 of engager button 152 with the threaded portion 138 of the bolt 128. Since the engager 142 interlocks the piston and bolt 128 for conjoint movement, piston 36 is also translated by rotation of knob 148. Movement of plunger 36 towards the distal end 40 of the syringe injects fluid into the catheter 42 and exerts a pressure on the syringe barrel 34 tending to move the barrel towards its distal end. The tendency of the barrel to move results in its flange 54 exerting a force proportional to the force within the syringe on an end of the sliding cylinder or annular member 26'. This force tends to translate member 26' in the direction of movement of the syringe plunger 36. This tendency to move is opposed by increased pressure within the reservoir 46', such pressure increase being displayed on the gauge 44.

After pressure within the syringe barrel 34 reaches a desired level, as indicated by gauge 44, the pressure is maintained at such level by frictional forces within the components of the drive mechanism 120. If necessary, knob 148 is slightly rotated to maintain the desired pressure level.

At the end of a dilation procedure, it is normally advisable to quickly deflate the catheter 42. For this purpose, the engagement portion 168 of the engager button 152 is moved in a downward direction, with respect to FIG. 9, to separate the raised portions 154 from the bolt 128. The bolt 128 is then translated with respect to the housing which results in quick withdrawal of the piston 36 from the syringe barrel 34. In this manner, pressure is quickly relieved within the catheter 42. Alternatively, pressure is reduced in a gradual manner by rotation of knob 148.

Previously, specific embodiments of the present invention have been described. It should be appreciated, however, that these embodiments have been described for the purposes of illustration only, without any intention of limiting the scope of the present invention. Rather, it is the intention that the present invention be limited only by the appended claims.

What is claimed is:

1. A pressure sensing device for measuring the fluid pressure in a closed system, the pressure in the closed system being varied by the movement of a syringe piston in a syringe barrel having a distal delivery end in fluid communication with the closed system, said pressure sensing device comprising:
    (a) a housing having a passageway extending therethrough for receiving a syringe barrel having a distal delivery end connectable to a closed system; and
    (b) pressure sensing means connected to said housing for sensing pressure changes in a fluid contained within the syringe barrel, said pressure sensing means including:
        (1) first means for sensing and for generating a signal representative of movement of the syringe barrel with respect to said housing, the syringe barrel being received in the housing in such manner that movement of the syringe barrel is proportional to pressure changes of a fluid contained within the syringe barrel; and
        (2) second means responsive to said first means for converting said signal into a pressure measurement.

2. The pressure sensing device of claim 1, further comprising a sliding cylinder supported for movement with respect to and positioned in said passageway, locking means connected to said housing for releasably interconnecting the syringe barrel and the housing, said sliding cylinder being positioned to receive therethrough the syringe barrel.

3. The pressure sensing device of claim 2, wherein said locking means includes a locking member connected to said housing adjacent said passageway, at least one of said locking member and syringe barrel being movable with respect to the other between a first position in which the syringe barrel is inserted into and removed from the housing and a second position in which said locking member prevents withdrawal of the syringe barrel from the housing.

4. The pressure sensing device of claim 1, further comprising a sliding, hollow cylinder supported within said passageway for movement with respect to said housing, said cylinder receiving therethrough the syringe barrel so that said cylinder is movable with said syringe barrel; and
    said first means of said pressure sensing means comprising a reservoir for a pressure transmitting fluid defined within said housing, said cylinder being operatively associated with the reservoir so that movement of said cylinder changes the pressure of fluid contained within the reservoir.

5. The pressure sensing device of claim 4, wherein said second means of said pressure sensing means comprises pressure gauge means for measuring fluid pressure in said reservoir.

6. The pressure sensing device of claim 5, wherein said reservoir is at least partially defined between an outer wall of said cylinder and a wall of said housing defining said passageway, said housing wall having a groove formed therein for receiving a seal, first seal means positioned in said housing wall groove for slidably sealingly engaging said outer cylinder wall to thereby form an end wall of said reservoir, said outer cylinder wall having a groove formed therein for receiving a seal, second seal means positioned in said outer cylinder wall groove for slidably sealingly engaging said housing wall to thereby form another end wall of said reservoir, said second seal means moving with said cylinder to thereby exert pressure on fluid contained in said reservoir.

7. The pressure sensing device of claim 1, wherein the syringe piston has an end thereof extending outside of the syringe barrel and wherein the device further comprises drive control means for controlling movement of the syringe piston with respect to the syringe barrel, said drive control means comprising:
    a second housing connected to said housing receiving the syringe barrel;
    a threaded member inserted into a passageway formed in said second housing, the passageway being parallel to the passageway receiving the syringe barrel;
    engagement means operatively associated with the passageway formed in said second housing for engaging the threaded member so that rotation of the threaded member results in controlled translation thereof; and
    means for interconnecting the threaded member with the end of the syringe piston outside the syringe barrel so that the piston and threaded member have conjoint translational movement.

8. The pressure sensing device of claim 7, wherein the engagement means is movable between a first position engaging the threaded member and a second position free from engagement with the threaded member.

9. A pressure sensing device for use with a surgical apparatus for dilating a vessel, the apparatus comprising an inflatable catheter insertable into a vessel to be dilated, a fluid for inflating the catheter, and a syringe connected to the catheter for forcing the fluid into the catheter, the syringe having a barrel containing the fluid and a piston movable in the barrel to force the fluid into the catheter to thereby increase fluid pressure and inflate the catheter, said pressure sensing device comprising:
    a housing having a longitudinally-extending passageway;

an open ended sliding cylinder mounted in said passageway for reciprocating movement with respect to said housing, said cylinder receiving said syringe barrel therein, said barrel having a delivery end connected to said catheter, and said cylinder or said barrel having means so that said cylinder is movable by said barrel;

means for sensing and for generating a signal representative of movement of said cylinder; and gauge means for displaying said signal, the relationship between said syringe barrel and said cylinder being such that movement of said syringe piston towards said delivery end results in proportional movement of said syringe barrel and said cylinder whereby the amount of movement of said cylinder is representative of changes in the fluid pressure in the catheter.

10. A pressure sensing device according to claim 9, further comprising:

a second housing connected to said housing receiving the syringe barrel;

a threaded member inserted into a second passageway defined by said second housing, said second passageway being parallel to the passageway receiving said cylinder;

engagement means operatively associated with said second passageway for engaging the threaded member so that rotation of the threaded member results in controlled translation thereof; and means for interconnecting the threaded member with the end of the syringe piston outside the syringe barrel so that the piston and threaded member have conjoint translational movement.

11. An angioplasty injector for dilating a tubular body member comprising:

an inflatable catheter insertable into a body member to be dilated;

a syringe having a barrel containing fluid for inflating the catheter and a syringe piston for controlling the forcing of fluid into the catheter;

a housing having a first passageway formed therein;

an annular member at least partially disposed within said first passageway, said annular member being supported for movement with respect to said housing and receiving therein the syringe barrel;

locking means connected to said housing for releasably holding said syringe barrel in said annular member;

a reservoir defined within said housing and at least partially encompassing said annular member in such manner that movement of said annular member results in pressure changes within said reservoir;

gauge means for displaying the pressure within said reservoir, said pressure being representative of the pressure of fluid in the syringe barrel;

means for defining a second passageway extending parallel to said first passageway;

a threaded member guided for movement in said second passageway;

engagement means for engaging said threaded member so that rotation of said threaded member translates said threaded member with respect to said housing; and means for interconnecting said threaded member and said syringe piston for conjoint movement so that rotation of said threaded member controls translation of said syringe piston.

12. A pressure sensing device for measuring the pressure in a closed system comprising:

a first housing having a wall defining a first passageway extending through said first housing;

a stepped hollow sliding cylinder positioned at least in part in said first passageway; said cylinder having an enlarged exterior diameter proximal portion guided for sliding movement by the wall of said first housing defining said first passageway and a reduced exterior diameter distal portion spaced from said first passageway defining wall to define an annular space therebetween, said first passageway defining wall having a portion at the distal end of said first passageway projecting inwardly towards said cylinder;

means for defining a reservoir within said housing comprising said annular space, a bore extending from said annular space to an exterior surface of said first housing, first seal means positioned adjacent said inwardly projecting portion of said first housing wall for slidably sealingly engaging said distal portion of said cylinder, second seal means positioned adjacent said proximal end of said cylinder and carried by said distal portion of said cylinder for slidably sealingly engaging said first passageway defining wall; and gauge means connected to said bore for measuring and displaying pressure of a fluid contained within said reservoir, said cylinder being movable with respect to said first housing to thereby vary pressure within said reservoir.

13. A pressure sensing device according to claim 12, further comprising locking means connected to said first housing adjacent to a proximal end of said cylinder for releasably interconnecting a syringe inserted through said cylinder to said housing, the syringe having a flange engageable with the proximal end of said cylinder for moving said cylinder with respect to said housing.

14. A pressure sensing device according to claim 12 or 13, wherein a syringe barrel containing fluid is positionable in said first passageway with a distal end of the barrel connected to a closed system and wherein a plunger is positionable in the barrel with an end thereof protruding from the barrel, said device further comprising:

a second housing connected to said first housing in such manner that a second passageway defined by said second housing is parallel with said first passageway;

an at least partially threaded bolt positioned in said second passageway;

engagement means carried by said second housing for engaging a threaded portion of said bolt so that rotation of said bolt translates said bolt with respect to said second housing; and means for interconnecting said bolt with an end of a plunger inserted into a barrel positioned in said cylinder so that said plunger has conjoint movement with said bolt, movement of said plunger into the barrel increasing fluid pressure within the barrel and closed system thereby exerting a force on the barrel so that the barrel and cylinder move with respect to said first housing thereby varying fluid pressure in said reservoir.

15. An injector for use in an angioplasty procedure, the injector controlling the rate and pressure of fluid injection in the angioplasty procedure and comprising:

housing means for defining first and second parallel passageways, the first passageway receiving a barrel of a syringe used in the angioplasty procedure, the syringe having a syringe piston disposed therein for controlling the rate and pressure of injection of fluid contained in the barrel;

a threaded member guided for movement in said second passageway;

engagement means carried by said housing means for engaging said threaded member so that rotation of said threaded member translates said threaded member with respect to said second passageway; and means for interconnecting said threaded member and the piston for conjoint movement in a first direction to increase pressure and in a direction opposite the first direction to decrease pressure in the fluid used in the angioplasty procedure, said means for interconnecting preventing independent movement of one of said piston and said threaded member with respect to the other.

16. An injector according to claim 14, wherein said engagement means is movable into a disengaged position in which said threaded member is translatable without rotation.

17. An injector according to claim 14, wherein said means for interconnecting has a first portion carried by and pivotally movable about one of said piston and said threaded member, and a second portion having a shaped recess designed to mate with an end of the other of said piston and said threaded member.

18. An injector according to one of claims 14, 15, or 16, further comprising a protective sleeve partially encompassing said threaded member, said sleeve extending through and being non-rotatable with respect to said second passageway, said sleeve having an opening formed therein so that a portion of said threaded member is engageable by said engagement means.

* * * * *